(12) United States Patent  (10) Patent No.: US 7,364,917 B2
Ichimura et al.  (45) Date of Patent: Apr. 29, 2008

(54) APPARATUS AND METHOD FOR DETECTING VAPORIZED GAS

(75) Inventors: Satoshi Ichimura, Hitachi (JP);
Masami Sakamoto, Hitachinaka (JP);
Toshio Iwasaki, Hitachi (JP)

(73) Assignee: Hitachi High-Tech Control Systems Corporation, Mito-shi (JP)

( * ) Notice: Subject to any disclaimer, the term of this patent is extended or adjusted under 35 U.S.C. 154(b) by 804 days.

(21) Appl. No.: 10/809,355

(22) Filed: Mar. 26, 2004

(65) Prior Publication Data

US 2004/0219067 A1   Nov. 4, 2004

(30) Foreign Application Priority Data

Mar. 31, 2003  (JP) ............................. 2003-093088

(51) Int. Cl.
*G01N 33/00* (2006.01)
(52) U.S. Cl. ................ 436/181; 422/50; 422/68.1; 422/78; 422/80; 422/82.01
(58) Field of Classification Search ............. 422/50, 422/68.1, 78, 80, 82.01; 436/181
See application file for complete search history.

(56) References Cited

U.S. PATENT DOCUMENTS

| 3,758,777 | A | 9/1973 | Brunnee et al. |
| 4,541,268 | A | 9/1985 | Odernheimer et al. ......... 73/23 |
| 5,212,991 | A | 5/1993 | Suzanne et al. |
| H1293 | H | 3/1994 | Carlon ....................... 73/23.2 |
| 5,425,263 | A | 6/1995 | Davies et al. .............. 73/28.05 |
| 5,552,600 | A | 9/1996 | Davies et al. |

FOREIGN PATENT DOCUMENTS

DE    2088055    6/1982
EP    0831319    3/1998

*Primary Examiner*—Jill Warden
*Assistant Examiner*—Samuel P Siefke
(74) *Attorney, Agent, or Firm*—Mattingly, Stanger, Malur & Brundidge, P.C.

(57) ABSTRACT

For detecting a component of a substance (of liquid or solid) on a front surface of a substrate, the substrate with the substance thereon is transferred into a vaporizing section, the substance is heated in the vaporizing section so that the component is vaporized from the substance in the vaporizing section, the component vaporized is fed from the substance in the vaporizing section to a detecting section, and the vaporized component is detected in the detecting section.

33 Claims, 7 Drawing Sheets

APPARATUS AND METHOD FOR DETECTING VAPORIZED GAS

BACKGROUND OF THE INVENTION

The present invention relates to an apparatus and method for detecting a component of a specimen of liquid or solid or the specimen itself by vaporizing the component of the specimen or the specimen itself.

In a conventional apparatus for analyzing a vapor from a sample as disclosed by U.S. Pat. No. 5,552,600, the sample is heated by a heater arranged at an upstream side in a carrier gas flow direction with respect to the sample, and a carrier gas flows through the sample to carry the vapor from the sample to an ionization/reaction region.

BRIEF SUMMARY OF THE INVENTION

An object of the present invention is to provide an apparatus and method for detecting a component of a substance or the substance itself by vaporizing the component of the substance or the substance itself, by which apparatus and method an accuracy of detecting the component of the substance or the substance itself is improved.

According to the invention, a method for detecting a component (including the substance itself) of a substance (of liquid or solid) on a front surface of a substrate, comprising the steps of: transferring the substrate with the substance thereon into a vaporizing section, heating the substance in the vaporizing section so that the component is vaporized from the substance in the vaporizing section, feeding the component vaporized from the substance in the vaporizing section to a detecting section, and detecting the vaporized component in the detecting section.

If in the step of feeding the component vaporized in the vaporizing section, a gaseous matter (may be the atmosphere or other than component(s) of the substance to be detected) other than the vaporized component is supplied toward the substance in the vaporizing section to be fed with the vaporized component toward the detecting section, the vaporization of the component is accelerated, and the vaporized component is stably fed toward the detecting section. If the gaseous matter is supplied toward the substance from a radially outer side with respect to the substance in a radially inward direction of the substance as seen in a stacking direction in which the substance and the substrate are stacked, the vaporized component is restrained from being discharged out of the vaporizing section without being fed toward the detecting section and/or from being diffused or distributed in all radial directions from a substantially radial center of the substance. If the gaseous matter is prevented from passing through the substrate in a stacking direction in which the substance and the substrate are stacked, the substrate is prevented from being cooled by the gaseous matter, and the vaporized component is restrained from being mixed with a component of the substrate. If the gaseous matter to be fed with the vaporized component from the vaporizing section toward the detecting section is prevented from being supplied to a reverse surface of the substrate opposite to the front surface in a stacking direction in which the substance and the substrate are stacked so that the gaseous matter is prevented from passing through the substrate in the stacking direction, the substrate is prevented from being unnecessarily cooled by the gaseous matter, and the vaporized component is restrained from being mixed with a component of the substrate.

If in the step of heating the substance, the substance is irradiated by a radiant heat energy to be heated so that the substance is prevented from being heated through the substrate in a stacking direction in which the substance and the substrate are stacked, the substrate is restrained from being unnecessarily heated.

If in the step of heating the substance, a reverse surface of the substrate opposite to the front surface in a stacking direction in which the substance and the substrate are stacked is heated by the heat energy with a contact thermal conduction on the reverse surface so the substance is heated from the reverse surface through the substrate in the stacking direction, the substance is heated with high heating efficiency.

If in the step of heating the substance, the substance is irradiated by a radiant heat energy to be heated so that the substance is prevented from being heated through the substrate in a stacking direction in which the substance and the substrate are stacked, and another heat energy is applied to a reverse surface of the substrate opposite to the front surface in the stacking direction so that the substance is heated from the reverse surface through the substrate in the stacking direction, the substance is heated with the highest heating efficiency.

If the method further comprises the step of changing a distance between the substrate and a heat source for generating a radiant heat energy to heat the substance so that an amount of the radiant heat energy per unit time period for heating the substance is changeable in accordance with a kind of the component to be detected, a plurality of the kinds of the component can be detected correctly with respective optimum temperature conditions or temperature changing manners. The changing of the distance may be performed before heating the substance and/or while heating the substance, in accordance with a kind of the component to be detected.

If in the step of detecting the vaporized component, a gaseous pressure in the detecting section is less than the atmospheric pressure, a partial pressure of the vaporized component is increased to be easily detected. If in the step of heating the substance, a gaseous pressure in the vaporizing section is less than the atmospheric pressure, the vaporization of the component is accelerated. If in the step of feeding the component, a gaseous pressure in the detecting section is less than a gaseous pressure in the vaporizing section, a flow of the vaporized component from the vaporizing section to the detecting section is accelerated.

If the method further comprises the step of removing the substrate from the vaporizing section after the step of heating the substance, and transferring another substrate with another substance thereon into the vaporizing section, According to the invention, an apparatus for detecting a component (including the substance itself) of a substance (of liquid or solid) on a front surface of a substrate, comprises, a vaporizing section including a substrate holder adapted to hold thereon the substrate with the substance thereon, a heater for generating a heat energy to heat the substance on the substrate held on the substrate holder so that the component is vaporized from the substance held on the substrate holder, and a detector for detecting the vaporized component.

If the vaporizing section includes an inlet port opening to supply a gaseous matter (may be the atmosphere or other than component(s) of the substance to be detected) other than the vaporized component for the substance held on the substrate holder so that the gaseous matter is fed with the vaporized component toward the detector, the vaporization of the component is accelerated, and the vaporized component is stably fed toward the detecting section.

If the inlet port is arranged to open at a radially outer side with respect to the substance on the substrate held on the substrate holder as seen in a stacking direction in which the substance and the substrate are stacked so that the gaseous matter is supplied toward the substance on the substrate held on the substrate holder in a radially inward direction of the substance as seen in the stacking direction, the vaporized component is restrained from being discharged out of the vaporizing section without being fed toward the detecting section and/or from being diffused or distributed in all radial directions from a substantially radial center of the substance. If the inlet port is arranged to prevent the gaseous matter from passing through the substrate held on the substrate holder in a stacking direction in which the substance and the substrate are stacked, the substrate is prevented from being cooled by the gaseous matter, and the vaporized component is restrained from being mixed with a component of the substrate. If the inlet port is arranged to prevent the gaseous matter to be fed with the vaporized component toward the detector from being supplied to a reverse surface of the substrate held on the substrate holder opposite to the front surface in a stacking direction in which the substance and the substrate are stacked, the substrate is prevented from being unnecessarily cooled by the gaseous matter, and the vaporized component is restrained from being mixed with a component of the substrate.

If the inlet port is capable of having an opening area sufficiently large for introducing the substrate from an outside of the apparatus onto the substrate holder through the opening area, a structure of the apparatus is significantly simplified although having the inlet port for introducing the gaseous matter into the apparatus.

If the inlet port is arranged to surround the front surface as seen in a stacking direction in which the substance and the substrate are stacked, the vaporized component is restrained from being diffused or distributed in a radial direction of the substance. If the inlet ports may include at least three sub-inlet ports arranged to surround the front surface as seen in the stacking direction. If the vaporizing section includes an outlet port through which the vaporized component is allowed to flow toward the detector, and the outlet port is surrounded by the inlet port as seen in the stacking direction, the vaporized component is securely guided toward the outlet port by the gaseous matter.

If the heater is capable of generating a radiant heat energy as the heat energy by which radiant heat energy the substance is irradiated to be heated so that the substance is prevented from being heated through the substrate in a stacking direction in which the substance and the substrate are stacked, the substrate is restrained from being unnecessarily heated.

If the heater is arranged to be contactable with a reverse surface are of the substrate held on the substrate holder opposite to the substance on the front surface in a stacking direction in which the substance and the substrate are stacked so that the substance is heated from the reverse surface through the substrate in the stacking direction with a contact thermal conduction between the heater and the reverse surface area, the substance is heated with high heating efficiency.

If the heater is capable of generating a radiant heat energy as the heat energy by which radiant heat energy the substance is irradiated to be heated so that the substance is prevented from being heated through the substrate in a stacking direction in which the substance and the substrate are stacked, and another heat energy to be applied to a reverse surface of the substrate held on the substrate holder opposite to the front surface in the stacking direction so that the substance is heated from the reverse surface through the substrate in the stacking direction, the substance is heated with the highest heating efficiency.

If at least one of the substrate holder and the heater capable of generating a radiant heat energy as the heat energy to heat the substance through irradiating the substance by the radiant heat energy and/or thermal conduction through the substrate whose reverse surface is irradiated by the radiant heat energy is movable to change a distance between the substrate and the heater so that an amount of the radiant heat energy per unit time period for heating the substance from the heater is changeable in accordance with a kind of the component to be detected, a plurality of the kinds of the component can be detected correctly with respective optimum temperature conditions or temperature changing manners. The distance is changeable before heating the substance and/or while heating the substance.

If the detector includes an exhausting device arranged at a downstream side in a flow direction of the vaporized component with respect to a position where the vaporized component is detected by the detector, to discharge the vaporized component to an outside of the apparatus in such a manner that a gaseous pressure at the position is less than the atmospheric pressure, a partial pressure of the vaporized component is increased to be easily detected. If the detector includes an exhausting device arranged at a downstream side in a flow direction of the vaporized component with respect to a position where the vaporized component is detected by the detector, to discharge the vaporized component to an outside of the apparatus in such a manner that a gaseous pressure on the substance on the substrate holder is less than the atmospheric pressure, the vaporization of the component is accelerated. If the detector includes an exhausting device arranged at a downstream side in a flow direction of the vaporized component with respect to a position where the vaporized component is detected by the detector, to discharge the vaporized component to an outside of the apparatus in such a manner that a gaseous pressure at the position is less than a gaseous pressure on the substance on the substrate holder, a flow of the vaporized component from the vaporizing section to the detector is accelerated.

If the vaporizing section includes an outlet port through which the vaporized component is allowed to flow toward the detector, and the heater is capable of generating (a radiant heat energy as) the heat energy (by which radiant heat energy the substance is irradiated) at an area (from which area the radiant heat energy is emitted to the substance) surrounding the outlet port as seen in a flow direction (of the vaporized gas) through the outlet port, the vaporized component is kept securely at a vapor condition to be restrained from being returned to a liquid or solid condition of the component by being cooled.

The vaporizing section may include a transfer member contactable with (and separable from) the substrate and movable with respect to the substrate holder so that the substrate supported by the transfer device is mounted onto the substrate holder and removed from the substrate holder. The transfer member may be capable of supporting thereon two of the substrates so that a mounting movement of one of the substrates toward the substrate holder and a removal movement of the other one of the substrates from the substrate holder occur simultaneously. The transfer member may include a hole and a projection to form a clearance between the hole and projection at two positions opposite to each other through the substance in a radial direction of the substrate in such a manner that the clearance is capable of receiving a part of the substrate to be compressed between the hole and projection to fix the part of the substrate and a tension is applied to another part of the substrate (on which the substance exists) between the two positions.

Other objects, features and advantages of the invention will become apparent from the following description of the embodiments of the invention taken in conjunction with the accompanying drawings.

DETAILED DESCRIPTION OF THE INVENTION

Figure 1:
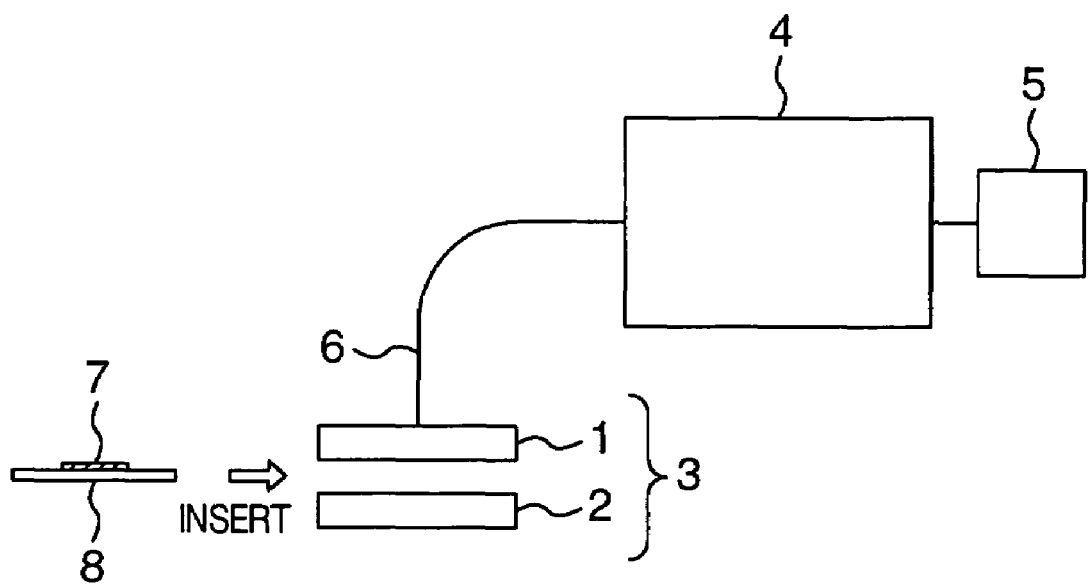
FIG. 1 is a schematic view of an apparatus for detecting a vapor of a component of a substance or the substance itself as a first embodiment of the invention.
Figure 2:
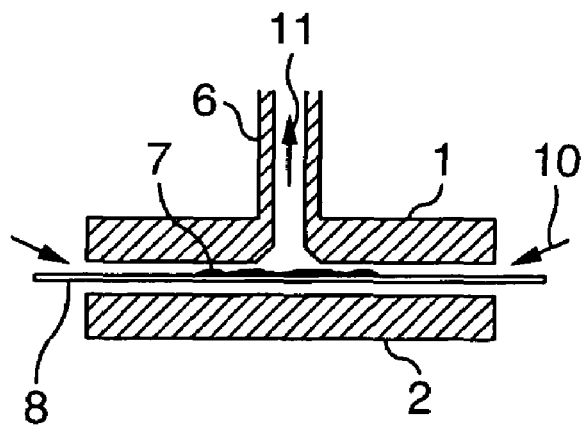
FIG. 2 is an enlarged cross sectional view showing a vaporizing section of the first embodiment.
Figure 3:
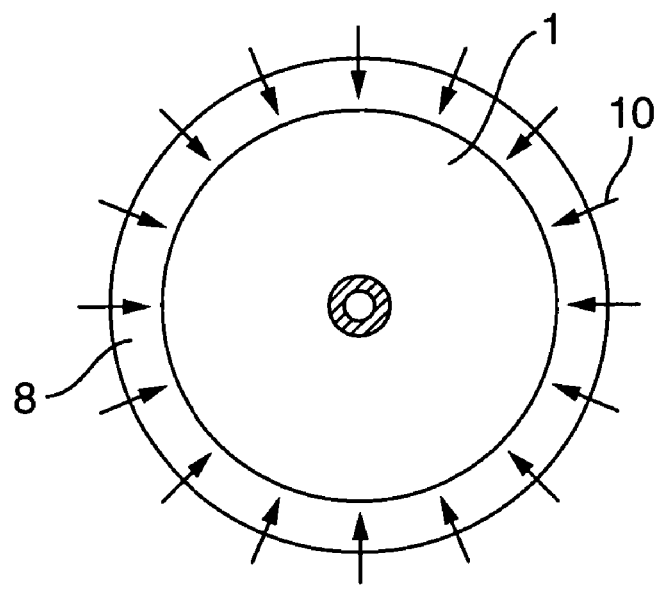
FIG. 3 is a view showing the vaporizing section of the first embodiment as seen in a direction perpendicular to a front surface of a substrate.

Hereafter, a first embodiment of the invention is described with reference to FIGS. 1-3. FIG. 1 is a broad construction view of a vaporized gas detecting apparatus as the first embodiment of the invention, FIG. 2 is a cross sectional view of an important part of the vaporized gas detecting apparatus shown in FIG. 1, and FIG. 3 is a plane view of the important part of the vaporized gas detecting apparatus shown in FIG. 1. As shown in FIG. 1, the vaporized gas detecting apparatus of the invention is constituted by a suction heating plate 1, an opposite heating plate 2 arranged at a lower position separated by a predetermined distance from the suction heating plate 1, a pipe 6 whose end is connected to the suction heating plate 1, a detecting means 4 connected to another end of the pipe 6, and an exhaust means 5 connected to the detecting means 4. And, a vaporizing means 3 is constituted by the suction heating plate 1 and the opposite heating plate 2.

A detecting operation in the above mentioned vaporized gas detecting apparatus is described below. The suction heating plate 1 and the opposite heating plate 2 are kept at a predetermined high temperature by a temperature adjusting means not shown. By exhausting the air from an interior of the detecting means 4 to less than the atmospheric pressure, the atmospheric gas is sucked through an opening of the vaporizing means connected to the interior of the detecting means 4 through the pipe 6, that is, between the suction heating plate 1 and the opposite heating plate 2.

A member 8 including an upper surface with a specimen 7 thereon is inserted horizontally by a transferring means not shown between the suction heating plate 1 and the opposite heating plate 2 to have a predetermined clearance between the upper surface and the suction heating plate 1. FIG. 2 and FIG. 3 are a cross sectional view and a plane view of the vicinity of the vaporizing means with the inserted member 8 therein.

By a thermal conduction or radiation from the suction heating plate 1 and the opposite heating plate 2 kept at the high temperature, the specimen 7 is heated to be vaporized so that a specimen gas is generated. On the other hand, by exhausting the air from the interior of the detecting means 4 to less than the atmospheric pressure, an atmospheric gas is sucked radially along the surface of the member 8 from the predetermined clearance. The atmospheric gas of a carrier gas 10 becomes a carrier gas 11 with the specimen gas flowing into the detecting means 4 through the pipe 6 to transfer the specimen gas. A component of the specimen gas is detected at the detecting means 4.

As described above, in the embodiment apparatus, since the atmospheric gas to be used as the carrier gas is sucked from the opening of the vaporizing means through which opening the member with the specimen is introduced, the opening does not need to be hermetically closed as being different from the vaporizing gas generating apparatus of the prior art. Therefore, a structure for hermetically closing the opening through which the member with the specimen is introduced is not necessary so that a degree of freedom for apparatus structure can be increased. Further, since a clearance is formed between the suction heating plate and the member to suck the atmospheric gas as the carrier gas 10 from the clearance, the member for holding thereon the specimen may be non-perforated. Further, since a gas flow course in the vicinity of the vaporizing means is not changed significantly in accordance with whether or not the member 8 is arranged in the vaporizing means, a gas flow is stable just after introducing the member 8 so that a reliability of detecting is improved.

Figure 4:
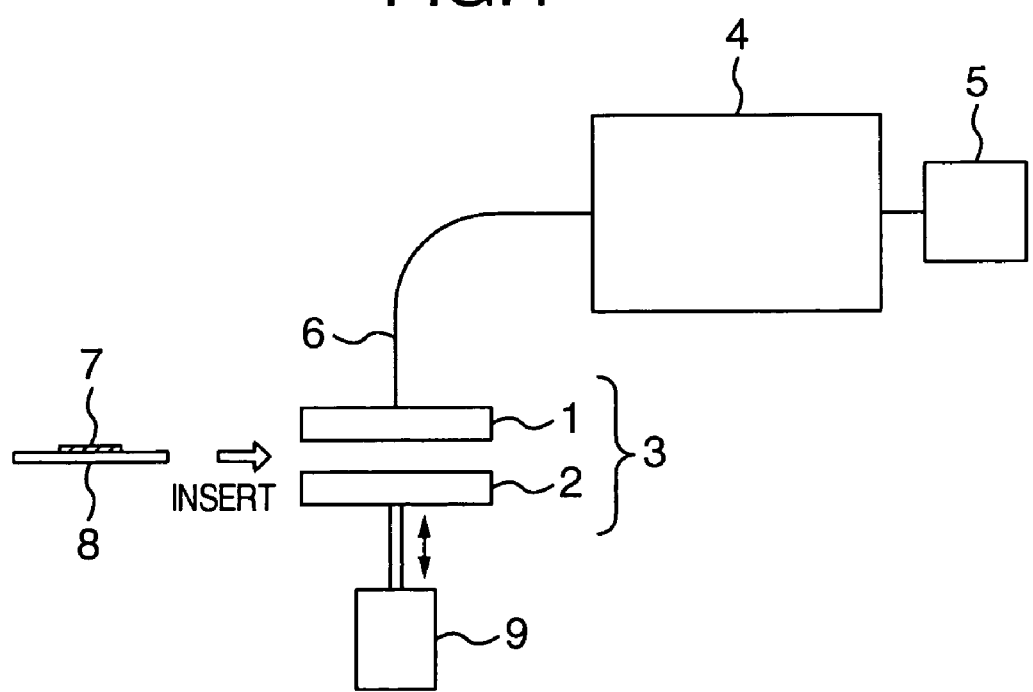
FIG. 4 is a schematic view of an apparatus for detecting a vapor of a component of a substance or the substance itself as a second embodiment of the invention.
Figure 5:
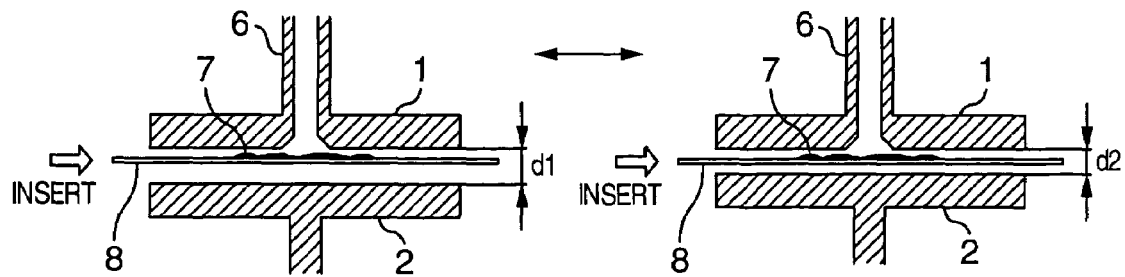
FIG. 5 includes enlarged cross sectional views showing a movement in the vaporizing section of the second embodiment.

Next, a second embodiment of the invention is described with reference to FIGS. 4-8. FIG. 4 is a broad construction view of a vaporized gas detecting apparatus as the second embodiment of the invention. The embodiment apparatus is differentiated from the first embodiment apparatus by that a driving device 9 is added, and the opposite heating plate 2 (and/or the suction heating plate 1) is movable by the driving device 9. Therefore, the distance between the suction heating plate 1 and the opposite heating plate 2 is changeable. FIG. 5 includes cross sectional views of the vicinity of the vaporizing means of the vaporized gas apparatus shown in FIG. 4 when the member with the specimen is incorporated, a left view shows a case in which the clearance between the suction heating plate 1 and the opposite heating plate 2 is a predetermined value d1, and a right view shows a case in which the clearance between the suction heating plate 1 and the opposite heating plate 2 is a value d2 smaller than d1.

A detecting operation of the above described vaporized gas detecting apparatus is described with reference to FIGS. 5-8. Incidentally, two kinds of materials different from each other in vapor pressure under common temperature (material A of a relatively higher vapor pressure, material B of a relatively lower vapor pressure) are included by the specimen 7 by respective predetermined amounts.

Figure 6A:
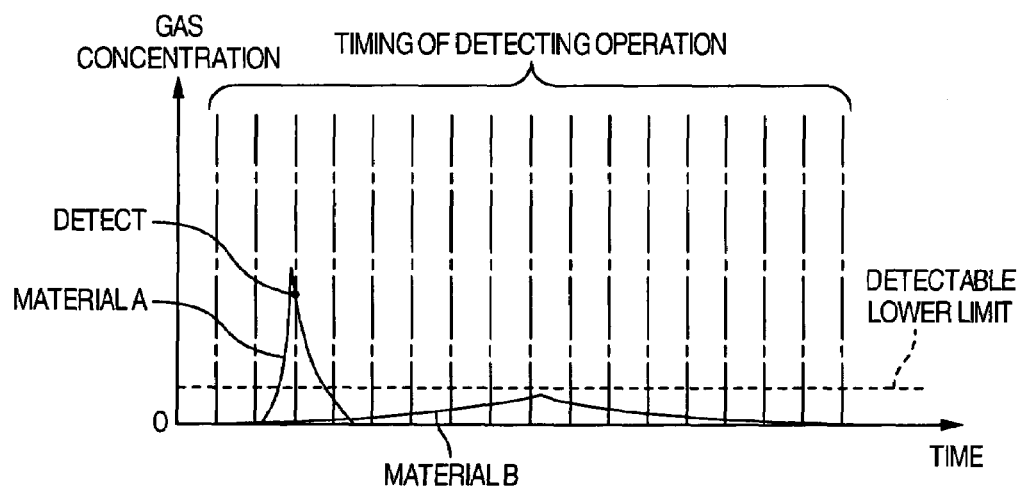
FIG. 6A is a diagram showing a relationship between a kind of the component or the substance itself, a detected concentration of the vaporized component or the vaporized substance itself, and a frequency of detecting the concentration in the second embodiment.

At first, a case in which the member 8 with the specimen 7 is introduced when the opposite heating plate 2 is fixed to a position shown in the left view of FIG. 5, that is, the distance between the suction heating plate 1 and the opposite heating plate 2 is fixed to the predetermined value d1 after the opposite heating plate 2 is vertically driven by the driving device 9 in FIG. 4 is described. A diagram of a concentration of the substance gas transferred from the vaporizing means to the interior of the detecting means along a time proceeding is shown in FIG. 6A. Incidentally in this diagram, zero value of the time proceeding is set when the member is introduced into the vaporizing means. Further, the gas concentrations are standardized by respective detecting lower limit values differentiated in accordance with the kinds of the substances. Under these standardizing, the detecting lower limit of constant value is shown by a dot line in the diagram. Generally, the detecting operation is carried out intermittently in the detecting means. Therefore, a timing of the intermittent detecting operation in the detecting means of the embodiment is shown by a dashed line in the diagram.

Generally, if the concentration of the substance gas introduced to the interior of the detecting means continuously exceeds the detecting lower limit for a time period longer than a cycle time period of the detecting operation, the substance can be detected at any of the detecting operation times. On the other hand, if the concentration of the substance gas does not exceed the detecting lower limit at each of the detecting operation times after the specimen is introduced, the substance cannot be detected. In FIG. 6A, the substance A corresponds to the former one, and the substance B corresponds to the latter one. A difference in gas concentration variation along the time proceeding in accordance with a difference in vapor pressure between the substances is caused by that the higher the vapor pressure of the substance is, the higher the vaporizing speed in the vaporizing means is, to generate the gas of high concentration is generated in a short time period, and the lower the vapor pressure of the substance is, the lower the vaporizing speed in the vaporizing means is, to generate the gas of low concentration is generated in a long time period.

Figure 6B:
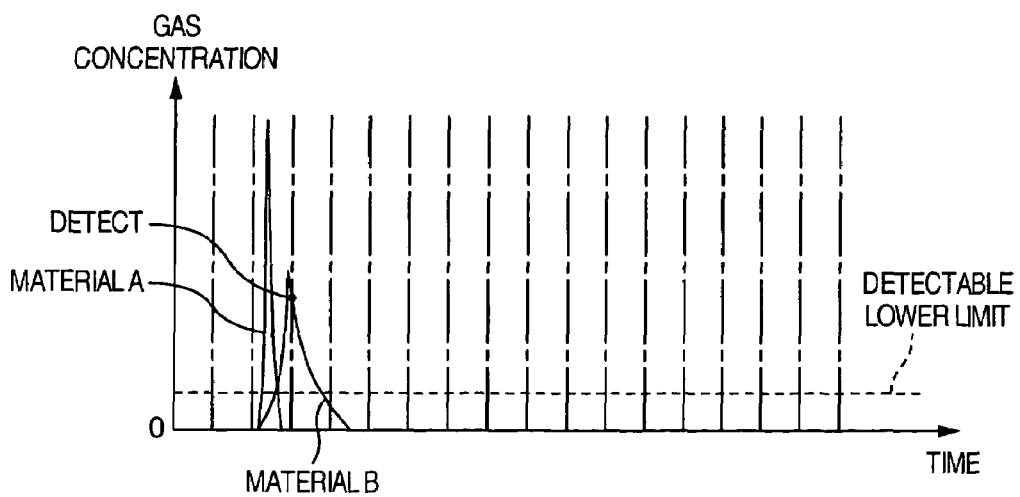
FIG. 6B is a diagram showing another relationship between a kind of the component or the substance itself, a detected concentration of the vaporized component or the vaporized substance itself, and a frequency of detecting the concentration in the second embodiment.

Next, a case in which the member 8 with the specimen 7 is introduced when the opposite heating plate 2 is fixed to a position shown in the right view of FIG. 5, that is, the distance between the suction heating plate 1 and the opposite heating plate 2 is fixed to the predetermined value d2 after the opposite heating plate 2 is vertically driven by the driving device 9 in FIG. 4 is described. A diagram of the concentration of the substance gas transferred from the vaporizing means to the interior of the detecting means along the time proceeding is shown in FIG. 6B. In comparison with FIG. 6A, a maximum value of the generated gas concentration of each of the substances A and B becomes greater and a generating time period becomes shorter, because the distance between the suction heating plate 1 and the opposite heating plate 2 is narrower to increase a speed of heating the specimen. In FIG. 6B, the substance B is detected, but the substance A whose vapor pressure is higher than the substance B is not detected, because the gas generation of the substance A is finalized in a time period shorter than the cycle time period of the detecting operation to depart from the detecting operation timing. If the opposite heating plate 2 contacts a surface of the member 8 having thereon no specimen 7, a heating speed becomes maximum.

As described above, in the embodiment apparatus, since the distance between the suction heating plate and the opposite heating plate is changeable by moving vertically the opposite heating plate by the driving device, the speed of heating the specimen in the vaporizing means is changeable. Therefore, the heating speed suitable for detecting the substance of the predetermined vapor pressure is easily obtainable.

Figure 7:
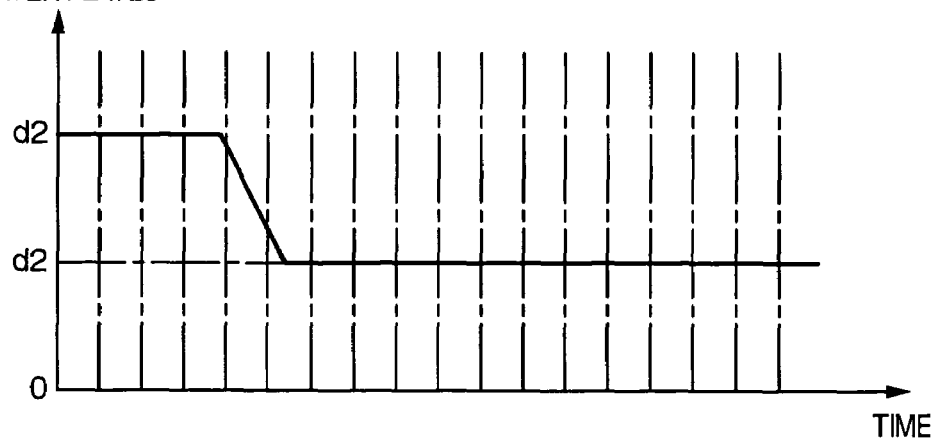
FIG. 7 is a diagram showing a relationship between a distance between heating plates and a time proceeding in the second embodiment.
Figure 8:
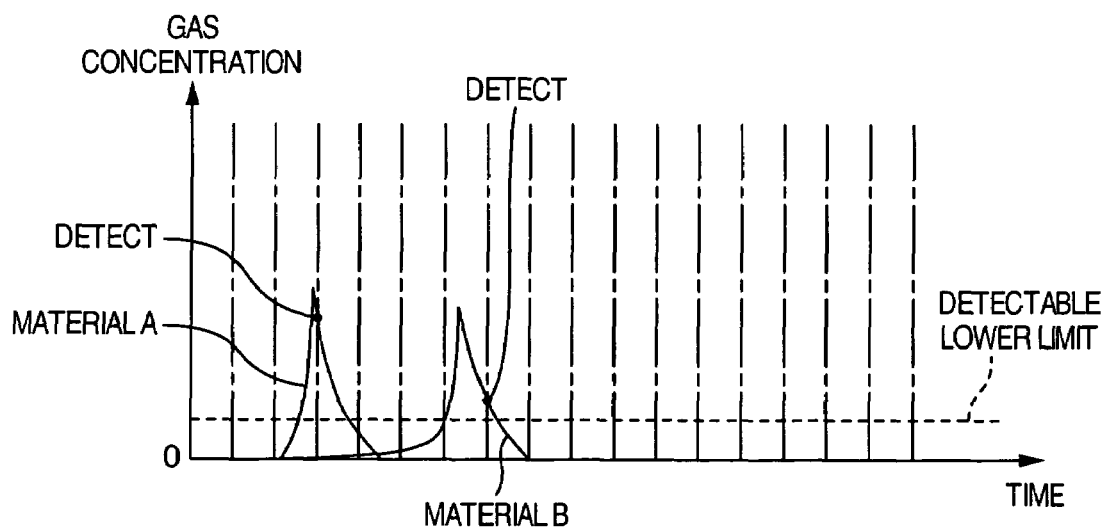
FIG. 8 is a diagram showing a relationship between a kind of the component of the substance itself, a detected concentration of the vaporized component or the vaporized substance itself, and a frequency of detecting the concentration in the second embodiment.

Next, a case in which after the condition shown in the left view of FIG. 5 is obtained when the member 8 with the specimen 7 is introduced, the condition shown in the right view of FIG. 5 is obtained by operating the driving device 9 to move the opposite heating plate upward in the embodiment apparatus shown in FIG. 4 is described. FIG. 7 shows a diagram of the distance between the suction heating plate and the opposite heating plate along the time proceeding in this case, and FIG. 8 shows a diagram of the concentration of the gas substance transferred to the interior of the detecting means along the time proceeding. The substance A is detected when the distance between the suction heating plate and the opposite heating plate is d1, and subsequently the substance B of the relatively lower vapor pressure is detected when the distance between the suction heating plate and the opposite heating plate is decreased to d2 by moving the opposite heating plate upward by the driving device to increase the heating speed. By decreasing the distance between the suction heating plate and the opposite heating plate to increase the heating speed after the specimen is introduced, various substances different in vapor pressures included by single specimen can be easily detected.

Figure 9:
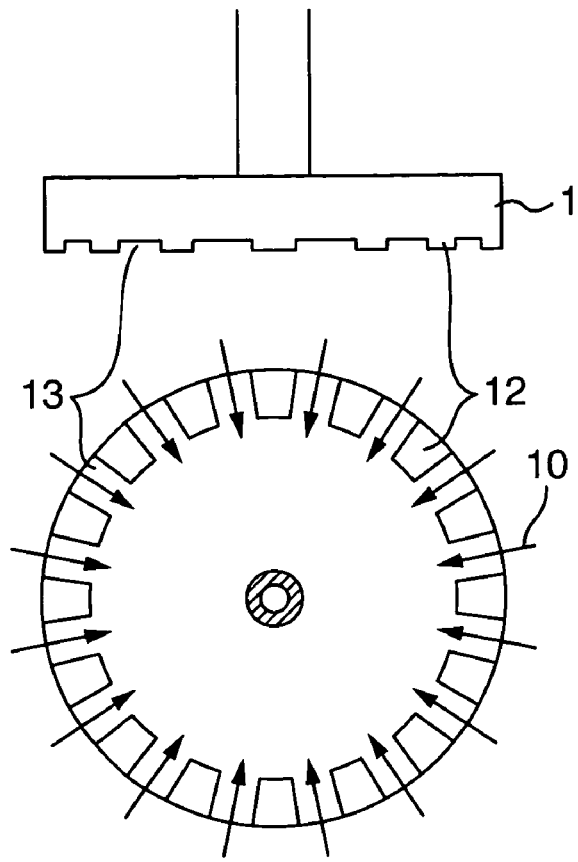
FIG. 9 includes a view showing the vaporizing section of the third embodiment as seen in the direction perpendicular to the front surface of the substrate, and a side view showing the vaporizing section of the third embodiment.
Figure 10:
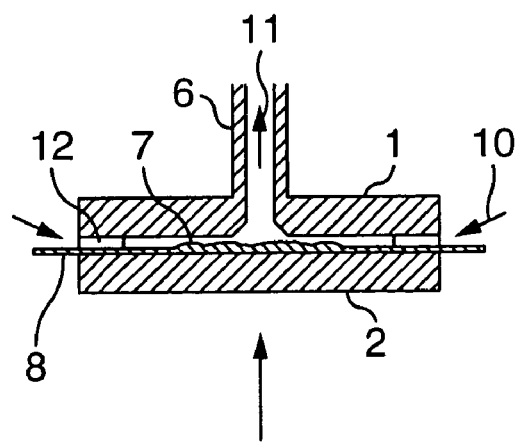
FIG. 10 is a cross sectional view showing the vaporizing section of the third embodiment.

Further, another embodiment of the vaporizing means is shown in FIGS. 9 and 10. In the embodiment, the member with the specimen thereon is clamped between the upper and lower heating plates to heat the specimen to be vaporized. A circumferential part of a heating surface of the suction heating plate 1 has a plurality of projections 12 of constant height circumferentially arranged around the center. Suction ports 13 of grooves are formed between the projections to suck the atmospheric gas. The suction ports 13 may have any shapes if a necessary flow rate to an interior part of the heating surface is kept. In response to introduction of the member with the specimen thereon under the suction heating plate 1, the opposite heating plate 2 moves upward to bring upward the member 8 into contact fixing with the suction heating plate 1. If the member 8 is soft for being held stably, a vicinity of a testing surface thereof is fixed to be held with a flat stable condition. If the carrier gas of the atmosphere is sucked in this condition, the carrier gas 10 is introduced from the suction ports 13 as clearances of the projections of the suction heating plate 1 to the interior of the heating surface so that the specimen 7 is vaporized to be introduced to the detector 4. Although the opposite heating plate 2 is flat to contact directly the member 8 so that the heating speed is increased in FIG. 10, the opposite heating plate 2 may have a concave shape (not shown) to form a distance with respect to the member 8 so that the heating speed is decreased. By fixing the member in this way, the significantly soft member can be held in flat condition to keep the clearance with respect to the heating members always constant so that the vaporization of the specimen is stable and the detection can be performed without scattering.

Figure 11:
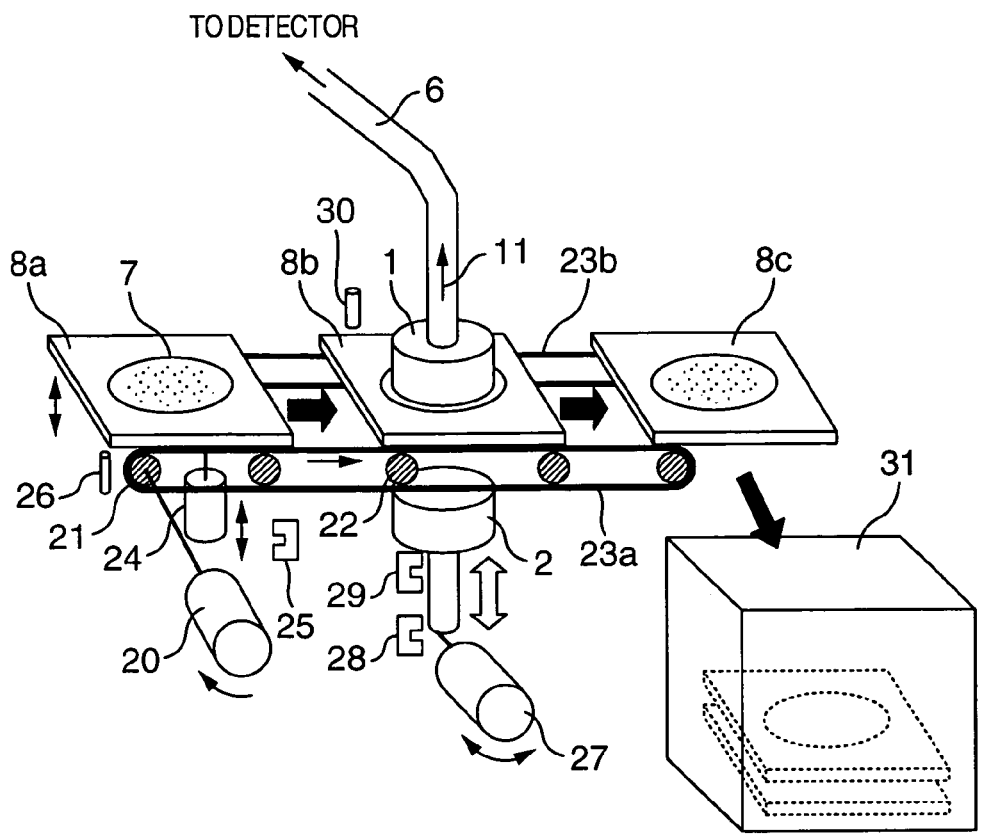
FIG. 11 is a schematic oblique projection view showing another apparatus for detecting the vapor of the component with a belt transfer member.

Next, an embodiment of transfer means is described. In FIG. 11, an entire structure of the transfer means is shown. In the structure, the vaporizing means as described above is arranged centrally, the member is introduced from a left side of the drawing to be transferred to the vaporizing means, and discharged to a right side of the drawing to be withdrawn. The detailed structure is described below. A member holding detector 26 detects whether or not the member 8a with the specimen 26 is held on a member vertically driving device 24. As a matter of course, if the member is reversed vertically or directed erroneously in a horizontal direction, it is not detected. The member 8 is positioned to be mounted onto transfer belts 23a and 23b by downward movement of the member vertically driving device 24, and is separated from the member vertically driving device 24 when the member vertically driving device 24 fully comes down. The downward movement is detected by a member descending detector 25. The member vertically driving device 24 is constructed by a solenoid, motor or air-cylinder. The transfer belts 23a and 23b are moved rotationally or parallel through a driving pulley 21 and driven pulleys 22 by a member transfer device 20. In the embodiment, the parallel movement is used for the member 8 to be measured at the vaporizing means and subsequently discharged. The transfer belts are preferably of rubber-type such as O-rings or band-belts to obtain a suitable friction. The member 8a on the transfer belts 23a and 23b is carried by the member transfer device 20 to the vaporizing means 3 and brought to standstill at a position between the suction heating plate 1 and the opposite heating plate 2. A member heating portion detector 30 detects whether or not a correct standstill thereof in the vaporizing means 3 has been obtained. On measuring, clearances among the member 8b, the suction heating plate 1 and the opposite heating plate 2 are kept constant by the upward movement of an opposite heating plate vertically driving device 27. A condition thereof is detected by an opposite heating plate ascent detector 29 when the opposite heating plate is ascending, and detected by an opposite heating plate decent detector 28 when the opposite heating plate is descending. The member transfer device 10 and opposite heating plate vertically driving device 27 are formed by solenoids, motors or air-cylinders, and AC servo-motors or pulse motors are effective for fine positioning or multi-points control. After measuring, the opposite heating plate vertically driving device 27 descends, and the member 8b is discharged to the right side of the drawing by the transfer belts 23a and 23b to be contained by a member recovery box 31. The transfer belts 23a and 23b can transfer simultaneously the member 8a to be measured now and the member 8b already measured.

The operation is described with reference to FIG. 11. At start, the member vertically driving device 24 exists at an upper portion to stand ready for mounting the member 8 thereon. When the member 8a is mounted, the member holding detector 26 detects the mounting of the member 8a. After detecting, the member vertically driving device 24 descends to mount the member 8a onto the transfer belts 23a and 23b. When the member vertically driving device 24 further descends to be separated from the member 8a, the member holding detector 26 becomes OFF so that the member vertically driving device 24 is stopped. In this time, a completion of the descent is detected by the member descending detector 25. The member 8a on the transfer belts 23a and 23b is moved by the member transfer device 20 to a predetermined position between the suction heating plate 1 and the opposite heating plate 2 of the vaporizing means 3. The member heating portion detector 30 detects a stop at the correct position. After the movement, the opposite heating plate 2 is moved upward by the opposite heating plate vertically driving device 27 to a predetermined distance with respect to the suction heating plate 1. The predetermined distance is obtainable by ON/OFF driving system when being fixed, or by a position control system when being variable, as shown in FIG. 5 or 9. The opposite heating plate ascent detector 29 detects a completion of the ascent to start the measuring. For a substance whose vaporizing speed is high, the measuring may be started just after the start of ascent of the opposite heating plate vertically driving device 27. After measuring the vaporization for some seconds to several dozen seconds, the opposite heating plate vertically driving device 27 descends to be confirmed by the opposite heating plate decent detector 28. Thereafter, the member 8b is discharged to the right side of the drawing by the transfer belts 23a and 23b to be contained by the member recovery box 31 so that the sequence is completed. By using the driving system and detector, these operations can be performed automatically. Here, since a next new member 8a may be set on the member vertically driving device 24 while vaporizing and measuring the member 8b, and the new member 8a may be moved to the vaporizing means simultaneously with discharging the member 8b after being measured, a significantly great time saving is obtainable. Further, since the already set member is recovered by the member recovery box 31, there is no necessity of awaiting the completion of the measuring. All may be recovered later. That is, there are effectiveness for improving a throughput because of no necessity of further operation other than continuous member setting, and effectiveness for improving operating efficiency because of no necessity of awaiting the recovery.

Figure 12:
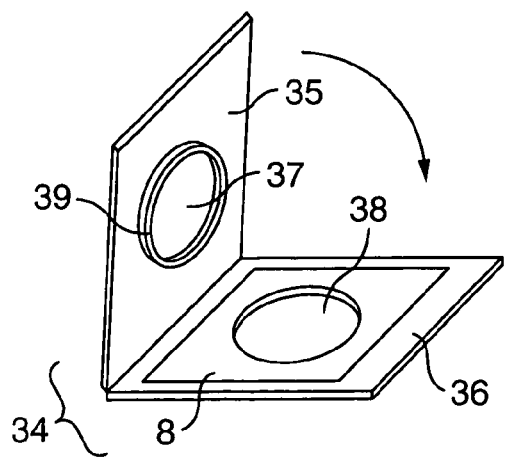
FIG. 12 is a schematic oblique projection view showing a substrate setting member.
Figure 13:
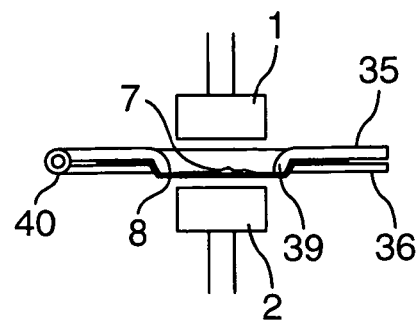
FIG. 13 is a cross sectional view showing the substrate setting member.

As another embodiment, a member setting element of the transfer means is shown in FIGS. 12 and 13. The setting member suitable for a case where the member 8 is significantly soft and a case where it is not suitable for being transferred is described below. The member setting element 34 includes upper and lower member setting elements 35 and 36 foldaway at a hinge 40 to clamp the member 8 therebetween. The setting element is made of a material having a thermal resistance and an appropriate frictional force with respect to the transfer belts 23a and 23b under repeated use. Holes 37 and 38 of dimensions for only heating the member 8 with the vaporizing means and preventing the member setting element 34 from being heated are formed on centers of the upper and lower member setting elements. Shapes of the holes may be circular or rectangular in accordance with the shape of the vaporizing means. The soft member 8 wrinkles when sweeping out the object so that the clearances with respect to the suction heating plate 1 and the opposite heating plate 2 can not be controlled, and whereby the correct measuring is not obtainable in addition to grinding the periphery to increase contaminant. Therefore, the upper member setting element 35 or member setting element 36 has a projection 38 to pull in the member 8 to be expanded. The projection 39 may be around the central hole 37 or 38 as shown, or arranged in an area of the member 8 to be expanded. As shown in FIG. 13, the member between the suction heating plate 1 and the opposite heating plate 2 is pulled in by the setting element and the projection to be expanded so that the distances among the member 8, the suction heating plate 1 and the opposite heating plate 2 are kept constant to enable a correct and reliable measuring. Further, there is an effect of decreasing the contaminant because of no necessity of grinding the periphery.

Figure 14:
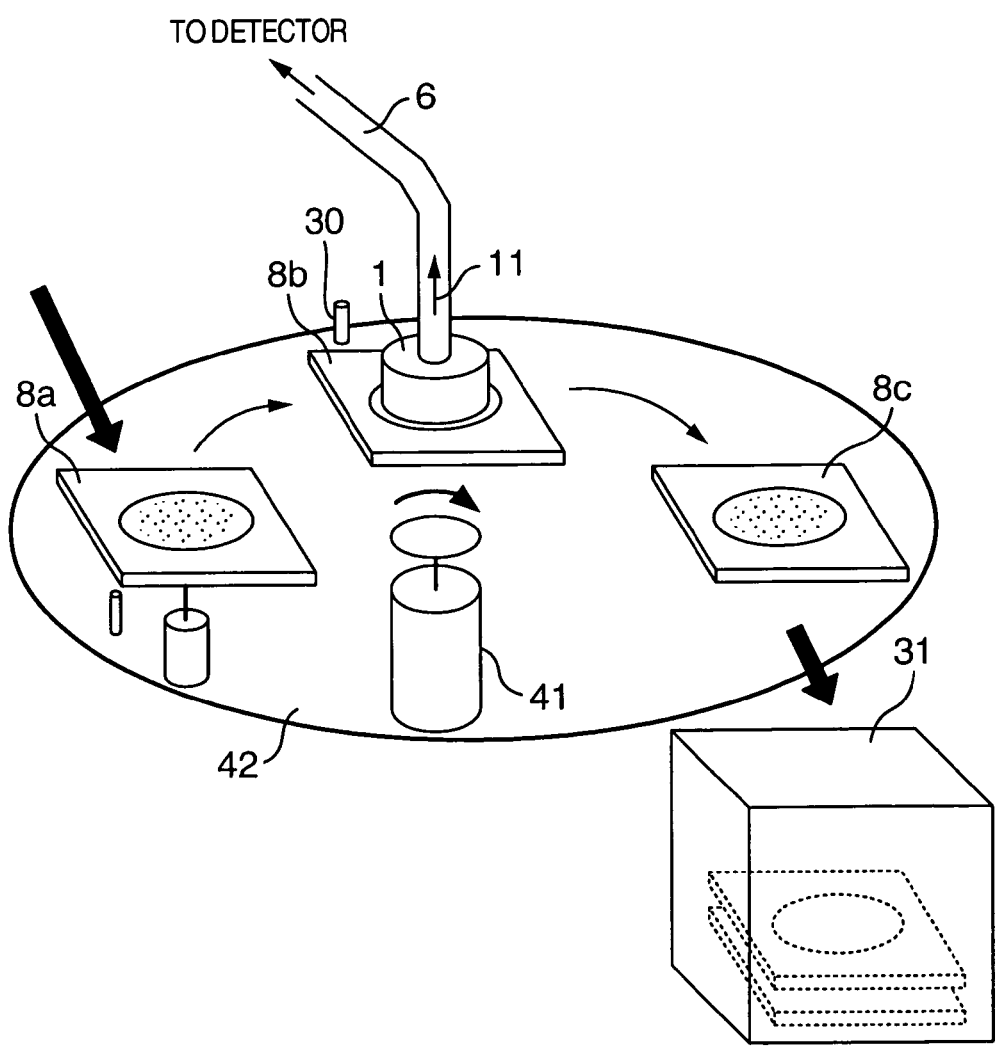
FIG. 14 is a schematic oblique projection view showing another apparatus for detecting the vapor of the component with a disk transfer member.

Another embodiment is shown in FIG. 14. in this, the transfer means is rotary type instead of straight type. A rotary plate 42 is used as a transfer medium instead of the transfer belt 32. The rotary plate 42 is driven by a rotary plate driving device 41 to transfer the member 8 from the member setting position through the vaporizing means 3 to the member recovery box. By making respective moving lengths equal to each other, the new member 8a and the member 8b after being measured can be transferred simultaneously as shown in FIG. 11 so that the same effect as FIG. 11 is obtainable. Which is used the straight transfer by the transfer belts or the rotary transfer by the rotary plate is determined appropriately with taking a space and structure of the apparatus into consideration.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A method for detecting a component of a substance on a front surface of a substrate, comprising the steps of:
   transferring the substrate with the substance thereon into a vaporizing section,
   heating the substance in the vaporizing section so that the component is vaporized from the substance in the vaporizing section,
   feeding the component vaporized from the substance in the vaporizing section to a detecting section, and
   detecting the vaporized component in the detecting section,
   wherein in the step of feeding the component vaporized in the vaporizing section, a gaseous matter other than the vaporized component is supplied toward the substance in the vaporizing section to be fed with the vaporized component toward the detecting section, and
   wherein the gaseous matter is supplied from a radially outer side with respect to the substance toward the substance in a radially inward direction of the substance as seen in a stacking direction in which the substance and the substrate are stacked.

2. A method according to claim 1, wherein the gaseous matter is prevented from passing through the substrate in a stacking direction in which the substance and the substrate are stacked.

3. A method according to claim 1, wherein the gaseous matter to be fed with the vaporized component from the vaporizing section toward the detecting section is prevented from being supplied to a reverse surface of the substrate opposite to the front surface in a stacking direction in which the substance and the substrate are stacked.

4. A method according to claim 1, wherein in the step of heating the substance, the substance is irradiated by a radiant heat energy to be heated so that the substance is prevented from being heated through the substrate in a stacking direction in which the substance and the substrate are stacked.

5. A method according to claim 1, wherein in the step of heating the substance, a reverse surface of the substrate opposite to the front surface in a stacking direction in which the substance and the substrate are stacked is heated by the heat energy with a contact thermal conduction on the reverse surface so the substance is heated from the reverse surface through the substrate in the stacking direction.

6. A method for detecting a component of a substance on a front surface of a substrate, comprising the steps of:
   transferring the substrate with the substance thereon into a vaporizing section,
   heating the substance in the vaporizing section so that the component is vaporized from the substance in the vaporizing section,
   feeding the component vaporized from the substance in the vaporizing section to a detecting section, and
   detecting the vaporized component in the detecting section,
   wherein in the step of heating the substance, the substance is irradiated by a radiant heat energy to be heated so that the substance is prevented from being heated through the substrate in a stacking direction in which the substance and the substrate are stacked, and another heat energy is applied to a reverse surface of the substrate opposite to the front surface in the stacking direction so that the substance is heated from the reverse surface through the substrate in the stacking direction.

7. A method for detecting a component of a substance on a front surface of a substrate, comprising the steps of:
   transferring the substrate with the substance thereon into a vaporizing section,
   heating the substance in the vaporizing section so that the component is vaporized from the substance in the vaporizing section,
   feeding the component vaporized from the substance in the vaporizing section to a detecting section,
   detecting the vaporized component in the detecting section, and
   changing a distance between the substrate and a heat source for generating a radiant heat energy to heat the substance so that an amount of the radiant heat energy per unit time period for heating the substance is changed.

8. A method according to claim 7, wherein the step of changing the distance is performed before heating the substance.

9. A method according to claim 7, wherein the step of changing the distance is performed while heating the substance.

10. A method for detecting a component of a substance on a front surface of a substrate, comprising the steps of:
    transferring the substrate with the substance thereon into a vaporizing section,
    heating the substance in the vaporizing section so that the component is vaporized from the substance in the vaporizing section, feeding the component vaporized from the substance in the vaporizing section to a detecting section, and detecting the vaporized component in the detecting section, wherein in the step of detecting the vaporized component, a gaseous pressure in the detecting section is less than the atmospheric pressure.

11. A method for detecting a component of a substance on a front surface of a substrate, comprising the steps of:

transferring the substrate with the substance thereon into a vaporizing section, heating the substance in the vaporizing section so that the component is vaporized from the substance in the vaporizing section, feeding the component vaporized from the substance in the vaporizing section to a detecting section, and detecting the vaporized component in the detecting section, wherein in the step of heating the substance, a gaseous pressure in the vaporizing section is less than the atmospheric pressure.

12. A method for detecting a component of a substance on a front surface of a substrate, comprising the steps of:

transferring the substrate with the substance thereon into a vaporizing section, heating the substance in the vaporizing section so that the component is vaporized from the substance in the vaporizing section, feeding the component vaporized from the substance in the vaporizing section to a detecting section, and detecting the vaporized component in the detecting section, wherein in the step of feeding the component, a gaseous pressure in the detecting section is less than a gaseous pressure in the vaporizing section.

13. A method according to claim 1, further comprising the step of removing the substrate from the vaporizing section after the step of heating the substance, and transferring another substrate with another substance thereon into the vaporizing section.

14. An apparatus for detecting a component of a substance on a front surface of a substrate, comprising, a vaporizing section including a substrate holder adapted to hold thereon the substrate with the substance thereon, a heater for generating a heat energy to heat the substance on the substrate held on the substrate holder so that the component is vaporized from the substance held on the substrate holder, and a detector for detecting the vaporized component, wherein the vaporizing section includes an inlet port opening to supply a gaseous matter other than the vaporized component for the substance held on the substrate holder so that the gaseous matter is fed with the vaporized component toward the detector, and wherein the inlet port is arranged to open at a radially outer side with respect to the substance on the substrate held on the substrate holder as seen in a stacking direction in which the substance and the substrate are stacked so that the gaseous matter is supplied toward the substance on the substrate held on the substrate holder in a radially inward direction of the substance as seen in the stacking direction.

15. An apparatus according to claim 14, wherein the inlet port is arranged to prevent the gaseous matter from passing through the substrate held on the substrate holder in a stacking direction in which the substance and the substrate are stacked.

16. An apparatus according to claim 14, wherein the inlet port is arranged to prevent the gaseous matter to be fed with the vaporized component toward the detector from being supplied to a reverse surface of the substrate held on the substrate holder opposite to the front surface in a stacking direction in which the substance and the substrate are stacked.

17. An apparatus for detecting a component of a substance on a front surface of a substrate, comprising, a vaporizing section including a substrate holder adapted to hold thereon the substrate with the substance thereon, a heater for generating a heat energy to heat the substance on the substrate held on the substrate holder so that the component is vaporized from the substance held on the substrate holder, and a detector for detecting the vaporized component, wherein the vaporizing section includes an inlet port opening to supply a gaseous matter other than the vaporized component for the substance held on the substrate holder so that the gaseous matter is fed with the vaporized component toward the detector, and wherein the inlet port is capable of having an opening area sufficiently large for introducing the substrate from an outside of the apparatus onto the substrate holder through the opening area.

18. An apparatus for detecting a component of a substance on a front surface of a substrate, comprising, a vaporizing section including a substrate holder adapted to hold thereon the substrate with the substance thereon, a heater for generating a heat energy to heat the substance on the substrate held on the substrate holder so that the component is vaporized from the substance held on the substrate holder, and a detector for detecting the vaporized component, wherein the vaporizing section includes an inlet port opening to supply a gaseous matter other than the vaporized component for the substance held on the substrate holder so that the gaseous matter is fed with the vaporized component toward the detector, and wherein the inlet port is arranged to surround the front surface as seen in a stacking direction in which the substance and the substrate are stacked.

19. An apparatus according to claim 18, wherein the inlet ports includes at least three sub-inlet ports arranged to surround the front surface as seen in the stacking direction.

20. An apparatus according to claim 18, wherein the vaporizing section includes an outlet port through which the vaporized component is allowed to flow toward the detector, and the outlet port is surrounded by the inlet port as seen in the stacking direction.

21. An apparatus for detecting a component of a substance on a front surface of a substrate, comprising, a vaporizing section including a substrate holder adapted to hold thereon the substrate with the substance thereon, a heater for generating a heat energy to heat the substance on the substrate held on the substrate holder so that the component is vaporized from the substance held on the substrate holder, and a detector for detecting the vaporized component, wherein the heater is capable of generating a radiant heat energy as the heat energy by which radiant heat energy the substance is irradiated to be heated so that the substance is prevented from being heated through the substrate in a stacking direction in which the substance and the substrate are stacked.

22. An apparatus according to claim 14, wherein the heater is arranged to be contactable with a reverse surface area of the substrate held on the substrate holder opposite to the substance on the front surface in a stacking direction in which the substance and the substrate are stacked so that the substance is heated from the reverse surface area through the substrate in the stacking direction with a contact thermal conduction between the heater and the reverse surface area.

23. An apparatus for detecting a component of a substance on a front surface of a substrate, comprising,
- a vaporizing section including a substrate holder adapted to hold thereon the substrate with the substance thereon,
- a heater for generating a heat energy to heat the substance on the substrate held on the substrate holder so that the component is vaporized from the substance held on the substrate holder, and
- a detector for detecting the vaporized component,
- wherein the heater is capable of generating a radiant heat energy as the heat energy by which radiant heat energy the substance is irradiated to be heated so that the substance is prevented from being heated through the substrate in a stacking direction in which the substance and the substrate are stacked, and another heat energy to be applied to a reverse surface of the substrate held on the substrate holder opposite to the front surface in the stacking direction so that the substance is heated from the reverse surface through the substrate in the stacking direction.

24. An apparatus for detecting a component of a substance on a front surface of a substrate, comprising,
- a vaporizing section including a substrate holder adapted to hold thereon the substrate with the substance thereon,
- a heater for generating a heat energy to heat the substance on the substrate held on the substrate holder so that the component is vaporized from the substance held on the substrate holder, and
- a detector for detecting the vaporized component,
- wherein at least one of the substrate holder and the heater capable of generating a radiant heat energy as the heat energy to heat the substance is movable to change a distance between the substrate and the heater so that an amount of the radiant heat energy per unit time period for heating the substance from the heater is changeable.

25. An apparatus according to claim 24, wherein the distance is changeable before heating the substance.

26. An apparatus according to claim 24, wherein the distance is changeable while heating the substance.

27. An apparatus for detecting a component of a substance on a front surface of a substrate, comprising,
- a vaporizing section including a substrate holder adapted to hold thereon the substrate with the substance thereon,
- a heater for generating a heat energy to heat the substance on the substrate held on the substrate holder so that the component is vaporized from the substance held on the substrate holder, and
- a detector for detecting the vaporized component,
- wherein the detector includes an exhausting device arranged at a downstream side in a flow direction of the vaporized component with respect to a position where the vaporized component is detected by the detector, to discharge the vaporized component to an outside of the apparatus in such a manner that a gaseous pressure at the position is less than the atmospheric pressure.

28. An apparatus for detecting a component of a substance on a front surface of a substrate, comprising,
- a vaporizing section including a substrate holder adapted to hold thereon the substrate with the substance thereon,
- a heater for generating a heat energy to heat the substance on the substrate held on the substrate holder so that the component is vaporized from the substance held on the substrate holder, and
- a detector for detecting the vaporized component,
- wherein the detector includes an exhausting device arranged at a downstream side in a flow direction of the vaporized component with respect to a position where the vaporized component is detected by the detector, to discharge the vaporized component to an outside of the apparatus in such a manner that a gaseous pressure on the substance on the substrate holder is less than the atmospheric pressure.

29. An apparatus for detecting a component of a substance on a front surface of a substrate, comprising,
- a vaporizing section including a substrate holder adapted to hold thereon the substrate with the substance thereon,
- a heater for generating a heat energy to heat the substance on the substrate held on the substrate holder so that the component is vaporized from the substance held on the substrate holder, and
- a detector for detecting the vaporized component,
- wherein the detector includes an exhausting device arranged at a downstream side in a flow direction of the vaporized component with respect to a position where the vaporized component is detected by the detector, to discharge the vaporized component to an outside of the apparatus in such a manner that a gaseous pressure at the position is less than a gaseous pressure on the substance on the substrate holder.

30. An apparatus according to claim 14, wherein the vaporizing section includes an outlet port through which the vaporized component is allowed to flow toward the detector, and the heater is capable of generating the heat energy at an area surrounding the outlet port as seen in a flow direction through the outlet port.

31. An apparatus for detecting a component of a substance on a front surface of a substrate, comprising,
- a vaporizing section including a substrate holder adapted to hold thereon the substrate with the substance thereon,
- a heater for generating a heat energy to heat the substance on the substrate held on the substrate holder so that the component is vaporized from the substance held on the substrate holder, and
- a detector for detecting the vaporized component,
- wherein the vaporizing section includes a transfer member contactable with the substrate and movable with respect to the substrate holder so that the substrate supported by the transfer device is mounted onto the substrate holder and removed from the substrate holder.

32. An apparatus according to claim 31, wherein the transfer member is capable of supporting thereon two of the substrates so that a movement of one of the substrates toward the substrate holder and a movement of the other one of the substrates from the substrate holder occur simultaneously.

33. An apparatus according to claim 31, wherein the transfer member includes a hole and a projection to form a clearance between the hole and projection in such a manner that the clearance is capable of receiving a part of the substrate to be compressed between the hole and projection.

* * * * *